(12) United States Patent
Schluter

(10) Patent No.: US 7,367,943 B2
(45) Date of Patent: May 6, 2008

(54) SYSTEMS AND METHODS FOR DETERMINING THE ELECTRICAL ACTIVITY OF A MATERIAL

(75) Inventor: Paul S. Schluter, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 756 days.

(21) Appl. No.: 10/752,448

(22) Filed: Jan. 6, 2004

(65) Prior Publication Data

US 2005/0154287 A1   Jul. 14, 2005

(51) Int. Cl.
- *A61B 8/00* (2006.01)
- *A61B 8/12* (2006.01)
- *A61B 8/14* (2006.01)

(52) U.S. Cl. .................. 600/438; 345/632; 607/60

(58) Field of Classification Search ........... 600/508, 600/509, 13
See application file for complete search history.

(56) References Cited

U.S. PATENT DOCUMENTS

| 5,594,849 A * | 1/1997 | Kuc et al. ............ 345/632 |
| 2002/0026224 A1 * | 2/2002 | Thompson et al. ...... 607/60 |

OTHER PUBLICATIONS

Montalibet et al., "Interaction Ultrasound-Magnetic Field: Experimental Setup And Detection Of The Interaction Current", 2000, IEEE Ultrasonics Symposium, pp. 533-536.*

* cited by examiner

*Primary Examiner*—Brian L. Casler
*Assistant Examiner*—Nasir Shahrestani

(57) ABSTRACT

The present description relates to a method comprising transmitting acoustic waves through a material of alternating electrical polarity to create a magnetic field and detecting the magnetic field.

16 Claims, 3 Drawing Sheets

SYSTEMS AND METHODS FOR DETERMINING THE ELECTRICAL ACTIVITY OF A MATERIAL

BACKGROUND

The present description relates generally to systems and methods for determining the electrical activity and/or properties of a material (e.g., biological tissue, etc.). In particular, the present description relates to systems and methods for noninvasively determining the electrical activity of heart tissue.

The standard 12-lead electrocardiogram (ECG) is a widely used noninvasive way of observing the electrical activity of the heart. For example, a physician may use the ECG to determine the underlying rhythm of the heart. The physician may also examine the characteristics of the ECG waveform to determine how electrical impulses are conducted through the heart.

Over the years a number of instruments have been developed in an attempt to more accurately determine the spatial and temporal electrical activity within the heart by solving the "inverse problem," i.e., determining the electrical source distribution within the heart that produces the set of signals observed on the surface of the body. Unfortunately, the "inverse problem" is difficult to solve because there are a large number of source distributions that can yield the same set of potentials when measured on the surface of the body with a set of electrodes. The problem is further complicated by the complex geometry and imprecisely known conductivities of the heart and surrounding tissue. Accordingly, it would be desirable to provide an improved noninvasive system and method for providing electrical information pertaining to a material and, in particular, a heart.

It should be understood that the claims define the scope of the subject matter for which protection is sought, regardless of whether any of the aforementioned disadvantages are overcome by the subject matter recited in the claims. Also, the terms recited in the claims should be given their ordinary and customary meaning as would be recognized by those of skill in the art, except, to the extent a term is used herein in a manner more expansive than its ordinary and customary meaning, the term should be given its ordinary and customary meaning plus the additional expansive meaning, or except if a term has been explicitly defined to have a different meaning by reciting the term followed by the phase "as used herein shall mean" or similar language. Accordingly, the claims are not tied to any particular embodiment, feature, or combination of features other than those explicitly recited in the claims.

SUMMARY

One embodiment relates to a method comprising transmitting acoustic waves through a material of alternating electrical polarity to create a magnetic field and detecting the magnetic field.

Another embodiment relates to a method comprising (a) insonating at least a portion of a heart and (b) detecting a magnetic field created by step (a).

Another embodiment relates to a method comprising transmitting acoustic waves through at least a portion of a heart and detecting a potential difference on a surface of a body which includes the heart. The potential difference having substantially the same frequency as the acoustic waves.

Another embodiment relates to a system comprising a computer, a transducer probe, and a receiver. The transducer probe is configured to transmit acoustic waves through a material of alternating electrical polarity. The transducer probe is coupled to the computer. The receiver is coupled to the computer. The receiver and computer are used to detect a magnetic field produced by transmitting the acoustic waves through the material.

DETAILED DESCRIPTION

The present description is generally provided in the context of a system which is configured to provide electrical information (e.g., activation times, lack of electrical activity, etc.) pertaining to a heart. Although, the present description is provided primarily in the context of providing electrical information pertaining to a heart, it should be understood that the systems and methods described herein may also be used in other contexts as would be recognized by those of ordinary skill. For example, the systems and methods described herein may be used to determine the electrical activity of other types of biological tissue other than the heart or to determine the electrical properties of any of a number of suitable materials that comprise portions of alternating polarity. It should also be understood that a particular example or embodiment described herein may be combined with one or more other examples or embodiments also described herein to form various additional embodiments as would be recognized by those of ordinary skill. Accordingly, the systems and methods described herein may be configured to form numerous embodiments and permutations as may be desired and/or recognized by those of ordinary skill.

Figure 1:
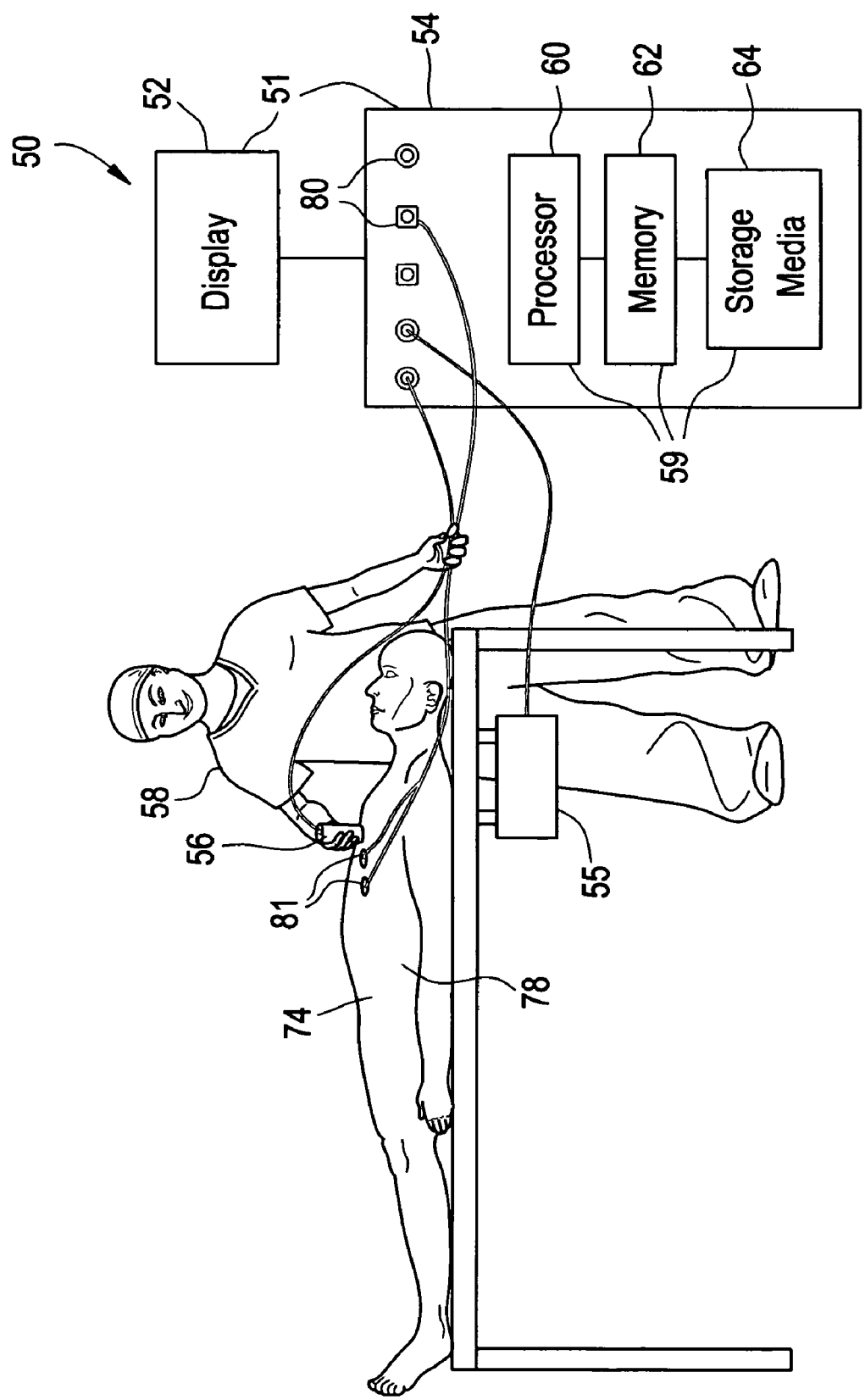
FIG. 1 shows a system for determining the electrical activity of a material according to one embodiment.
Figure 2:
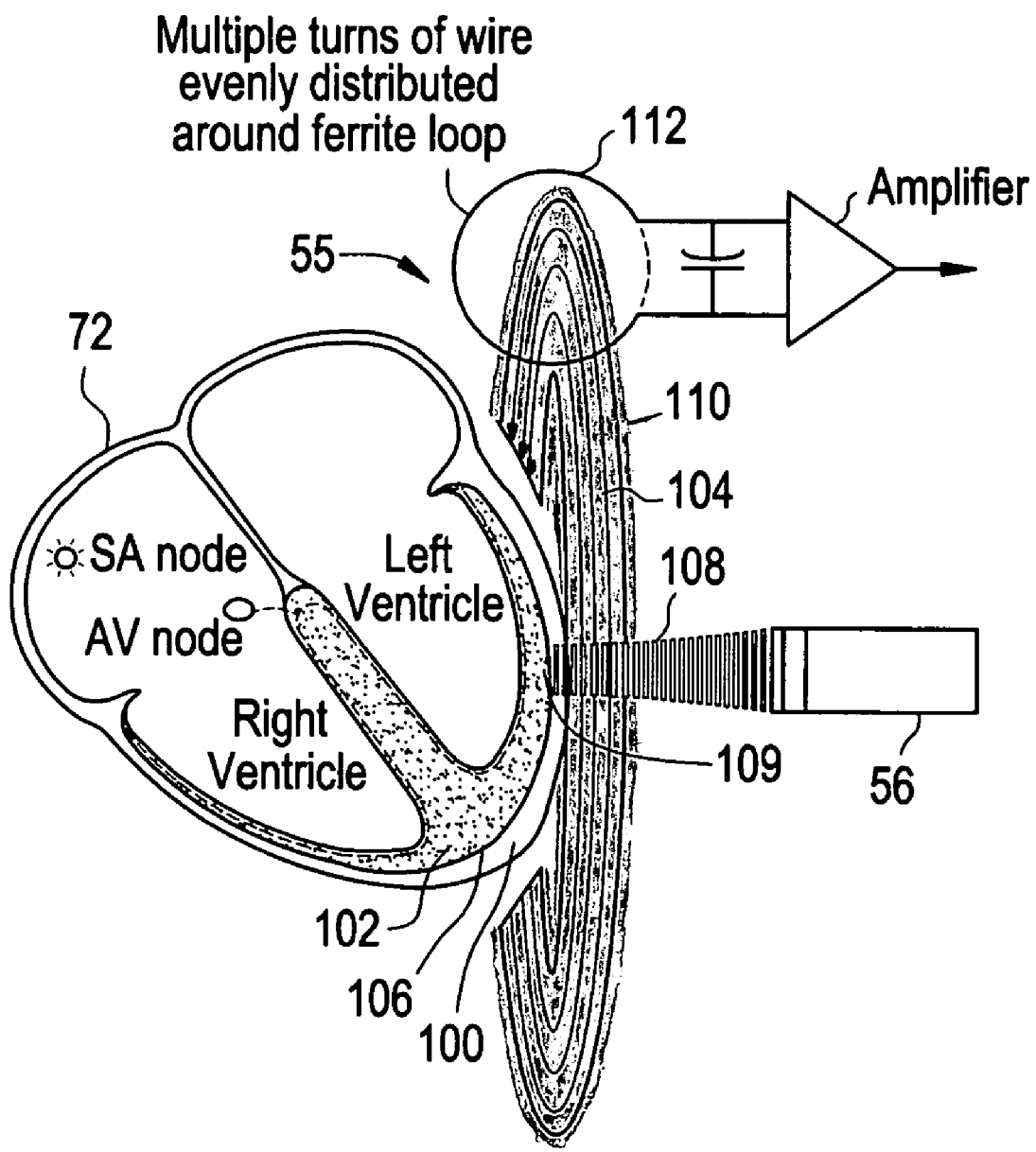
FIG. 2 shows a diagram of one embodiment of a system for determining the electrical activity of a heart.

Referring to FIGS. 1 and 2, one embodiment of a system 50 is shown. System 50 includes a console or computer 51 and a transducer probe 56. System 50, broadly described, uses ultrasonic waves to determine a variety of information (e.g., electrical and/or structural information pertaining to a heart 72 or other organs and/or structures inside the body of a patient 74, etc.) pertaining to patient 74.

System 50 may be any one of a wide variety of suitable systems used for an equally wide variety of uses. For example, in one embodiment, system 50 may be any system that is configured to use acoustic waves to determine the electrical activity and/or structural properties of an organ or structure in the body of patient 74. In another embodiment, system 50 may be an electrophysiology (EP) monitoring and diagnostic system that is configured to use transducer probe 56 to provide electrical and/or structural information pertaining to heart 72 (e.g., to assist in guiding a probe to a location on heart 72 that is to be ablated).

As shown in FIG. 1, transducer probe 56, receiver 55, and display 52 are communicatively coupled to computer components 59 in cabinet 54. Information sensed by transducer probe 56 and received by receiver 55 may be communicated to computer components 59. Information from computer components 59 may then be communicated to display 52 where it is displayed to a nearby person 58 (e.g., attending physician, nurse, technician, etc.). The configuration shown in FIG. 1 is only one of many suitable configurations. For example, in another embodiment, transducer probe 56 and/or receiver 55 may be communicatively coupled directly to display 52. In this embodiment, display 52 may be configured to display the information provided by transducer probe 56 without the information being communicated through cabinet 54 (e.g., display 52 comprises the necessary computer components 59 to receive information from probe 56). In another embodiment, display 52 may be combined with cabinet 54 so that the functions generally performed by computer components 59 in cabinet 54 and display 52 are performed by the combined unit (e.g., display 52 comprises all of computer components 59). In another embodiment, console 51 may include two or more displays 52. The displays may be used to display electrical information pertaining to heart 72 or other types of information (e.g., electrocardiogram (ECG) signals, ultrasound images, etc.). In one embodiment, display 52 may be configured to be in a position that is convenient for person 58 to view (e.g., at height of person 58's eyes as person 58 is standing, etc.) as person 58 moves transducer probe 56.

Cabinet 54, shown in FIG. 1, comprises computer components 59 such as a processor 60, memory 62, storage media 64, and one or more input devices (e.g., mouse, keyboard, etc.). Computer components 59 are generally configured to receive information from transducer probe 56 and receiver 55, process the information, and provide output (e.g., a structural image of heart 72, an electrical map of heart 72, etc.) using display 52. Storage media 64 may be any one of a number of suitable storage devices including an optical storage disk such as a CD, DVD, a high performance magneto optical disk, a magnetic disk, etc. In general, storage media 64 differs from memory 62 in that storage media 64 is configured to maintain the information even when storage media 64 is not provided with power. In contrast, memory 62 typically does not maintain the information when the power is off.

Display 52, shown in FIG. 1, is configured to provide output to a user in the form of information, which may include alphanumeric (e.g., text, numbers, etc.) output, graphical image output, etc. In one embodiment, display 52 may be configured to also receive input from a user (e.g., touch screen, buttons located adjacent to the screen portion of display 52, etc.). Display 52 may be any number of suitable displays in any number of suitable configurations. For example, display 52 may be a liquid crystal display, flat screen display, SVGA display, VGA display, etc.

In one embodiment, display 52 may be configured to display one or more structural representations of heart 72 such as images (computed tomography, magnetic resonance, ultrasound, etc.), models, etc. Display 52 may also be configured to display an electrical map of heart 72 produced using electrical information acquired with transducer probe 56 and receiver 55 as explained in greater detail below. In another embodiment, display 52 may be configured to simultaneously display an ultrasound image of heart 72 and electrical information acquired using transducer probe 56. In a further embodiment, the electrical information is overlaid the ultrasound image on display 52. In particular, display 52 may be configured to simultaneously display an ultrasound image of heart 72 and the activation times for at least a portion of heart 72 with the activation times overlaying the image. In general, the activation times correspond to the portion of heart 72 that is overlaid by the particular activation time (e.g., a map is created having contour lines showing the activation times of various portions of heart 72, etc.).

Display 52 may also be configured to display one or more representations of one or more catheters inserted into heart 72. The catheters inside heart 72 may be used to deactivate certain portions of heart 72 (e.g., ablation of an area causing an arrhythmia, etc.). In one embodiment, the position of the catheter inside heart 72 may be determined using transducer probe 56. A representation of the catheter can then be shown in the resulting ultrasound image. In another embodiment, the position of the catheter inside heart 72 may be determined using a localization system. The position of the probe may then be registered to the structural representation of heart 72 (e.g., CT, MR, or ultrasound image, etc.) and/or corresponding electrical information (i.e., the electrical information as determined using transducer probe 56) shown on display 52.

In one embodiment, console 51 is a desktop computer which is configured to perform ultrasound imaging procedures. In another embodiment, console 51 may be configured to include input receivers 80 that are configured to receive additional information pertaining to patient 74. For example, in one embodiment, one or more input receivers 80 may be configured to receive input from electrocardiogram leads 81, which are attached to skin surface 78.

In general, transducer probe 56 is configured to transmit high frequency (e.g., typically above approximately twenty thousand hertz) acoustic waves 108 into the body of patient 74. Acoustic waves 108 travel through the body of patient 74 and hit boundaries between tissues (e.g., between fluid and soft tissue, soft tissue and bone, etc.). At each boundary some of acoustic waves 108 are reflected back to transducer probe 56. The reflected waves are sensed by probe 56 and the information is relayed to computer components 59. Processor 60 calculates the distance from probe 56 to the tissue or organ based on the time at which each echo returns and the speed of sound in tissue. This structural information provided by transducer 56 may be used to create an image of at least a portion of the inside of the body of patient 74. Display 52 may then be configured to display an ultrasound image showing the distance and intensities of the echoes. In various embodiments, the ultrasound image may be two, three, or four dimensional. Transducer probe 56 may also be any suitable shape and size and may be a single element probe or a multiple element probe.

System 50 typically includes transducer controls (not shown). The transducer controls allow the user to adjust the amplitude, frequency, and duration of the pulses emitted from transducer probe 56. System 50 may also include additional components and systems. For example, system 50 may comprise a printer. System 50 may also be configured as part of a network of computers (e.g., wireless, cabled, secure network, etc.) or as a stand-alone system. In situations where system 50 is part of a network, information pertaining to patient 74 may be transmitted over the network to the data record for patient 74.

Referring to FIG. 2, in one embodiment, system 50 is configured to use ultrasonic acoustic waves 108 to determine the electrical activity of heart 72. Acoustic waves 108 create a weak magnetic field 104 through compression and rarefaction of a polarized boundary 106 between a nondepolarized portion 100 of heart 72 and a depolarized portion 102 of heart 72. Magnetic field 104 is detected by receiver 55 and used to provide electrical information pertaining to heart 72. The electrical information may assist the physician or other person (e.g., technician, etc.) to recognize problems with heart 72 such as myocardial ischemia and infarct, as well as to identify and locate cardiac tissue that may need to be removed or deactivated to suppress certain arrhythmias.

As shown in FIG. 2, receiver 55 is positioned coaxially with transducer probe 56. Generally, when receiver 55 is positioned coaxially with transducer probe 56, a ferrite loop antenna 110 is aligned to receive the greatest magnetic flux arising from the insonated region 109 of heart 72. Other alternatives may also be used. For example, as shown in FIG. 1, receiver 55 is fixed to the underside of a table which patient 74 is laying on.

Figure 3:
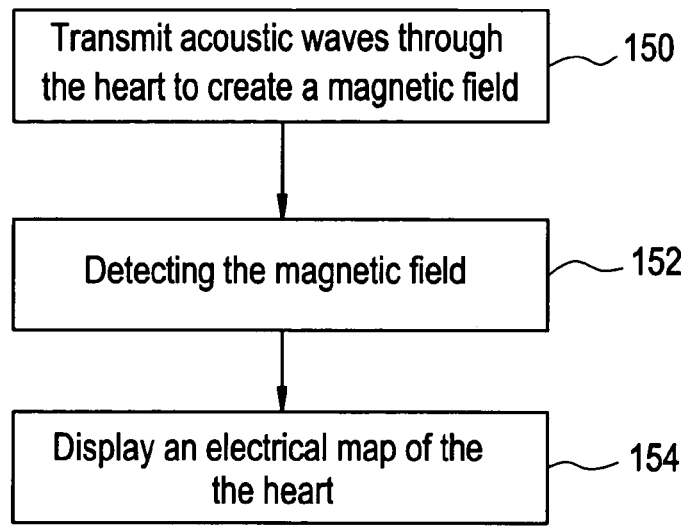
FIG. 3 shows a flow chart of a method for determining the electrical activity of a heart according to one embodiment.

Referring to FIG. 3, one embodiment of a method is shown for determining the electrical activity of a material using acoustic waves. In general, the method comprises steps 150, 152, and 154, which include, respectively: transmitting acoustic waves through heart 72 to create a magnetic field, detecting the magnetic field, and displaying the electrical depolarization of heart 72.

At step 150, acoustic waves 108 are transmitted through heart 72, or, in other words, heart 72 is insonated. In this embodiment, the wave-averaged intensity I(SPPA) of acoustic waves 108 is at least approximately 250 Watts/cm$^2$, or, desirably, at least approximately 300 Watts/cm$^2$, or, suitably, at least approximately 350 Watts/cm$^2$. It should be noted that various regulations may apply to the intensity of acoustic waves 108 that may be used to insonate various organs or structures inside the body. The instantaneous energy (i) is related to the acoustic pressure (p) by equation (1).

$$i = p^2/\rho c \tag{1}$$

For purposes of the following calculations, the instantaneous energy (i) is assumed to be 350 Watts/cm$^2$. The calculations described herein may be repeated for other instantaneous energy values. In equation (1), c is the speed of sound in tissue, which is approximately 1540 m/sec and $\rho$ is the density of "average" tissue, which is approximately 1060 kg/m$^3$. Using these values, equation (1) can be solved for p to yield an acoustic pressure of approximately 2.4 MPascals.

The acoustic pressure p may then be used to estimate the "strain" or compression of the heart tissue as acoustic waves 108 propagate through it. Equation (2) relates the square of the speed of sound c through any medium to the change in pressure and density in the medium.

$$c^2 = \partial p(\text{change in pressure})/\partial p(\text{change in density}) \tag{2}$$

When $\partial p$ is approximately 2.4 MPa and c$^2$=(1540 M/sec)$^2$ for tissue, equation (2) may be solved to obtain a $\partial p$ of approximately 1.01 kg/m$^3$. The displacement (strain) $\partial x/x$ may be obtained by dividing the change in density (approximately 1.01 kg/m$^3$) by the density of average tissue (approximately 1060 kg/m$^3$) to yield a displacement of approximately 9.5×10$^{-4}$, or approximately 0.1%, for a one-dimensional longitudinal acoustic wave 108.

Polarized boundary 106 between depolarized portion 102 and nondepolarized portion 100 may be modeled as a polarized capacitance. Once the polarization charge and the thickness of the polarized boundary 106 are known, the strength of the Hertzian current dipole due to the compression and rarefaction can be determined.

The potential difference between depolarized portion 102 and nondepolarized portion 100 of heart 72 is approximately 40 mV, which is less than the −90 to +20 mV intra- to extra-cellular voltage difference measured for an individual cardiac muscle cell. The net charge per unit area for polarized boundary 106 can be estimated by using a nominal cell membrane capacitance of 1 $\mu$F/cm$^2$, resulting in a charge q=40 mV*1 $\mu$F/cm$^2$, or 0.04 $\mu$Coulombs/cm$^2$.

The diameter of acoustic waves 108 at polarized boundary 106 are approximately five millimeters. In other embodiments, acoustic waves 108 may be any of a number of suitable sizes. A typical embodiment of system 50 may be capable of providing resolutions below at least one millimeter. Acoustic waves 108 having a diameter of approximately five millimeters have an area of approximately 0.20 cm$^2$ and insonate a total charge of 0.20 cm$^2$*0.04 $\mu$Coulombs/cm$^2$, which is 0.008 $\mu$Coulombs. Using the displacement strain $\partial x/x$ of 9.5×10$^{-4}$, the total time varying charge dQ' is dQ'=9.5×10$^{-4}$*0.008 $\mu$Coulombs=7.6×10$^{-12}$ Coulombs. For acoustic waves with a frequency of approximately 1 MHz, the current (i) in polarized boundary 106 is i=dQ'/dt=7.6×10$^{-12}$ Coulombs/10$^{-6}$ sec=7.6 $\mu$A.

The thickness, h, of polarized boundary 106 (i.e. the gap between depolarized portion 102 and nondepolarized portion 100 of heart 72) may be determined as follows. The rapid depolarization phase (Phase 0) takes less than 100 $\mu$sec to complete. Assuming that the depolarization propagation velocity is 0.5 meter/second for ventricular muscle tissue, then 50 $\mu$m of tissue is traversed during the time between the nondepolarized and depolarized states. This is consistent with the observation that the axial length of the cardiac muscle fibers is 100 $\mu$m. Accordingly, a thickness, h, of polarized boundary 106 of approximately 100 $\mu$m is used for the calculations that follow. This distance is less than one-quarter the 1.5 mm wavelength of 1 MHz acoustic waves 108.

In summary, the following parameters may be used to determine the magnetic field for a Hertzian dipole:

| | |
|---|---|
| Dipole current | $I_0$ = 7.6 $\mu$A |
| Dipole spacing (thickness h) | h = 100 $\mu$m |
| Frequency | f = 1 MHz |

The magnetic field for a Hertzian dipole radiator may be calculated using equation (3):

$$H_\phi = \frac{I_0 h}{4\pi} e^{-jkr}\left(\frac{jk}{r} + \frac{1}{r^2}\right)\sin\theta \tag{3}$$

where, $$j = \sqrt{-1}$$

$$k = \omega/\upsilon = \omega\sqrt{\mu\epsilon} = 2\pi/\lambda$$

Figure 4:
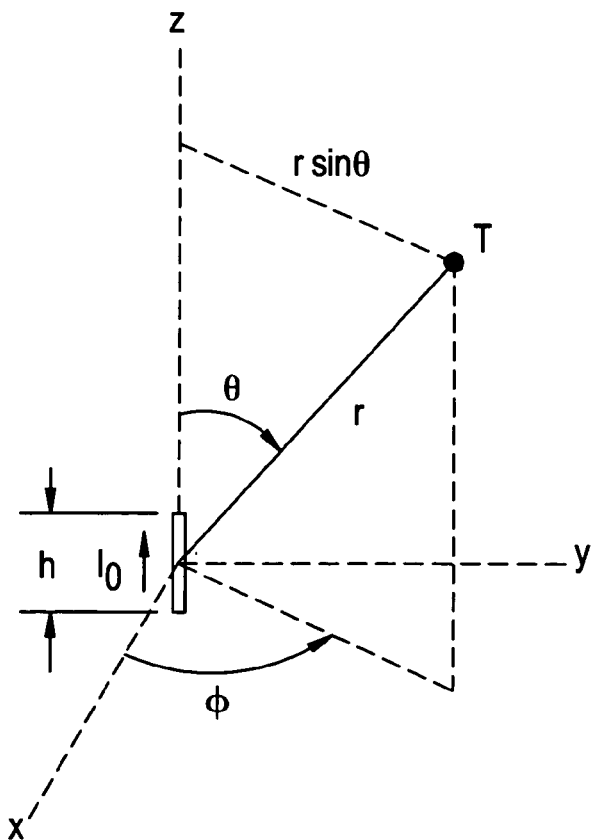
FIG. 4 shows a spatial diagram of the relationship between the position of a receiver and a dipole current created using acoustic waves according to one embodiment.

$\phi$, $\theta$ and r specify measurement point T shown in FIG. 4; and z is aligned along the axis of acoustic waves 108.

FIG. 4 is a diagram of the relationship between point T and dipole current $I_0$. As shown in FIG. 4, point T represents the position of receiver 55 in relation to dipole current $I_0$. In general, dipole current $I_0$ is aligned in a vertical axis z. The thickness of polarized boundary 106 is h. Point T is located a distance r from the center of dipole current $I_0$ where $\theta$ and $\phi$ represent the angles at which a line extending from dipole current $I_0$ to point T deviates from axis z and axis x, respectively.

Using only the "near-field" 1/r$^2$ term, magnetic field 104 is very nearly in phase with the current. $H_\phi$ may be identified as the usual induction field obtained from Ampere's law, $|H_\phi|=I_0$ h $\sin/4\pi r^2$. Locating the receiver 55 at $\theta=45°$ and distance r=0.1 meters, $|H_\phi|=4.3\times10^{-9}$ A/m. Magnetic field 104 is $B=\mu_0$ $H=4\pi\times10^{-7}$ H/m*$4.3\times10^{-9}$ A/m=$5.4\times10^{-15}$ Tesla.

At step 152 in FIG. 3, magnetic field 104 is detected. Although the strength of magnetic field 104 is relatively small, it may be detected using an RF receiver that operates at room temperature. In one embodiment, an AM receiver may be used to detect magnetic field 104. The AM receiver may be configured to use a ferrite bar antenna having an electric field sensitivity of 1 μV/meter with a Signal to Noise Ratio (SNR) that is typically $\geqq 20$ dB. The ferrite bar antenna detects and measures magnetic field 104. For a wave propagating through free space, the magnetic field, H, is H= $\sqrt{\epsilon/\mu_0}E=E/376\Omega$ Amps/meter. A 1 μV/meter electric field provides a magnetic field induction of H=$2.6\times10^{-9}$ A/m and a magnetic field strength B=$\mu_0$H=$3.34\times10^{-15}$ Tesla. These levels are comparable to magnetic field 104 produced by the Hertzian dipole and indicate that conventional RF receiver technology may be used to detect magnetic field 104.

In another embodiment, the SNR may be improved by using a ferrite loop antenna 110 to "capture" more of the magnetic flux produced by the Hertzian dipole. One desirable orientation for the ferrite loop antenna 110 is collinear with the propagation direction of acoustic waves 108. The toroidal geometry of ferrite loop antenna 110 captures the flux due to $H_\phi$ generated by the Hertzian dipole but is relatively immune to other external magnetic fields.

For ferrite rods, the "gain" provided by the enhanced permeability of the ferrite material varies linearly with the "effective" $\mu_{eff}$ of the rod. The $\mu_{eff}$ of the rod is somewhat less than the actual permeability $\mu_r$ of the ferrite and incorporates the leakage flux that is largely dependent on the geometry of the rod. For a toroidal ferrite core, many of the same principles apply, and a ferrite material can be selected that will provide a $\mu_{eff}$ of 200$\mu_0$.

Using a $\mu_{eff}$ of 200 $\mu_0$ and a magnetic induction, calculated above, of $H_\phi=4.3\times10^{-9}$ A/m, the magnetic flux $B_\phi=\mu_{eff}$ $H_\phi=200\mu_{101}$ $H_{100}=200*4\pi\times10^{-7}$ H/m*$4.3\times10^{-9}$ A/m, or $B_{\phi, ferrite}=1.08\times10^{-12}$ Tesla. The total magnetic flux $\psi$ through the rod is $B_{\phi, ferrite}$ times the cross-sectional area of the ferrite. A 1.25 cm diameter ferrite rod has a cross sectional area of $1.56\times10^{-4}$ m$^2$ and would have a total flux of $1.68\times10^{-16}$ Tesla-m$^2$.

The rate-of-change of flux, $\partial\psi/\partial t$, is sensed by a coil of wire 112 wrapped around the toroidal ferrite. The voltage across the coil 112 is $V_{coil}=\partial\psi/\partial t*N$ where N is the number of turns of wire. Letting N=50, $V_{coil}=1.68\times10^{-16}$ Tesla-m$^2$*$1\times10^{+6}$ sec$^{-1}$*$50=8.4\times10^{-9}$ volts (8.4 nV). The SNR may be improved by using a capacitor C positioned in parallel with the inductance L of coil 112 which is wrapped around the ferrite rod. A "quality factor" Q of 100 may be achieved for the resonant circuit formed by L and C, yielding a bandwidth of 10 KHz. Assuming the front end electronics has a voltage noise $V_n=1$ nV/$\sqrt{Hz}$ (using the Analog Devices AD797 ultra-low noise amplifier) an SNR is obtained as shown in equation (4).

$$SNR = V_{coil}*Q/V_n * \sqrt{BW(Hz)} = 8.4\text{ nV}*100/(1\text{ nV}/\sqrt{Hz} * \sqrt{10000\text{ Hz}}) = 8.4. \quad (4)$$

In this manner, magnetic field 104 may be detected using antenna 110.

At step 154, an electrical map of heart 72 is displayed on display 52. The electrical map is created using magnetic field 104 detected by receiver 55. The electrical map may show information such as infarcted tissue by its lack of electrical activity. In one embodiment, electrical map is displayed on an "A-mode" (amplitude mode), "B-mode" (brightness mode), and "M-mode" (motion mode) display that is associated with a nonscanning single channel probe 56. In another embodiment, electrical map is displayed on a two dimensional "B-mode" display that is associated with a scanning two dimensional probe 56. In another embodiment, electrical map is displayed on a system that creates three dimensional reconstructions from registered two dimensional "B-mode" scans.

In the previous example, acoustic waves 108 had a frequency of approximately 1 MHz. However, in other embodiments, the frequency of acoustic waves 108 may be increased, for example, to provide an increased transient response. For example, in order to provide increased transient response, the frequency may be 5 MHz and the geometry and permeability of the ferrite core may be optimized. In other embodiments, the frequency may be 4 MHz to 6 MHz or 1 MHz to 10 MHz.

In another embodiment, system 50 may use a SQUID (Superconducting QUantum Interference Detector) to measure magnetic flux through ferrite loop antenna 110, rather than using a coil. Ferrite loop antenna 110 would still be used to "collect" the flux and concentrate it in a small gap that accommodates the SQUID device.

In another embodiment the system 50 may be configured to detect electrical potentials on skin surface 78 of patient 74 (e.g., ECG leads). The electrical potentials from the hertzian dipole have substantially the same frequency as acoustic waves 108. The electrical potentials may be used to create an electrical map of heart 72 in a manner that is analogous to using and measuring the magnetic field created by insonating dipole boundary 106 described previously.

The construction and arrangement of the elements described herein are illustrative only. Although only a few embodiments have been described in detail in this disclosure, those of ordinary skill who review this disclosure will readily appreciate that many modifications are possible without departing from the spirit of the subject matter disclosed herein. Accordingly, all such modifications are intended to be included within the scope of the methods and systems described herein. The order or sequence of any process or method steps may be varied or re-sequenced according to alternative embodiments. Other substitutions, modifications, changes and omissions may be made in the design, operating conditions and arrangement of the embodiments without departing from the spirit and scope of the methods and systems described herein.

What is claimed is:

1. A method to map a biological tissue of alternating electrical polarity, the method comprising the steps of:
    transmitting a plurality of acoustic waves at a frequency though the biological tissue of alternating electrical polarity having a boundary between a depolarized portion and a nondepolarized portion;
    detecting a variation in a magnetic field generated in response to the plurality of acoustic waves causing compression and rarefaction of the boundary;
    measuring the variation in the magnetic field at the frequency of the plurality of acoustic waves;

translating the variation in the magnetic field at the frequency to a map of an electrical activity of the material; and generating a display illustrative of the electrical activity of the biological tissue.

2. The method of claim 1, further comprising the step of measuring a variation in an electrical potential at substantially the same frequency as the plurality of acoustic waves, the variation in electrical potential correlated to the variation in the magnetic field from the compression and rarefaction of the boundary caused by the plurality of acoustic waves.

3. The method of claim 1, wherein the step of transmitting the plurality of acoustic waves is from a transducer probe, and further including the step of detecting reflection of the plurality of acoustic waves at the transducer probe in response to the transmitting step, and translating reflection of the plurality of acoustic waves to create an ultrasound image.

4. The method of claim 1, wherein the biological tissue comprises a heart.

5. The method of claim 1, wherein the display includes a map of the variation in the magnetic field in response to the step of transmitting the plurality of acoustic waves combined with an ultrasound image illustrative of a structural representation of the biological tissue, the ultrasound image acquired via a transducer probe transmitting the plurality of acoustic waves.

6. The method of claim 5, wherein the plurality of acoustic waves are transmitted from an ultrasound probe of an ultrasound imaging system, and wherein the generating step includes generating a structural representation of the biological tissue using the plurality of acoustic waves.

7. The method of claim 1, wherein a majority of the acoustic waves have a frequency of not less than twenty thousand hertz, and wherein the steps of detecting and translating the variation in the magnetic field is at the frequency of not less than twenty thousand hertz.

8. The method of claim 1, wherein the acoustic waves are transmitted from a transducer probe, and further comprising the step of positioning a receiver coaxially with the transducer probe, the receiver operable to detect the variation in the magnetic field.

9. A system, comprising:
a transducer probe configured to transmit a plurality of acoustic waves at a frequency through a biological tissue of alternating electrical polarity having a boundary between a depolarized portion and a non-depolarized portion;

a receiver operable to detect a variation in an magnetic field generated in response to the plurality of the acoustic waves causing compression and rarefaction of the boundary, the receiver configured to detect the variation in the magnetic field at a frequency substantially same to the frequency of the plurality of acoustic waves transmitted;

a computer in communication with the transducer probe and the receiver, the computer operable to translate the variation in the magnetic field at the frequency to a map of an electrical activity of the biological tissue; and a display in communication with the computer, the display operable to illustrate the map of the electrical activity of the biological tissue.

10. The system of claim 9, wherein the display includes a map illustrative of the variation in the electrical activity overlying a structural representation of the biological tissue generated from the plurality of acoustic waves from the transducer probe.

11. The system of claim 9, wherein the display includes a structural representation of the material generated from the plurality of acoustic waves transmitted from the transducer probe.

12. The system of claim 9, wherein the biological tissue is part of a heart.

13. The system of claim 9, wherein the system is configured to measure a variation in a potential difference at a substantially same frequency of the frequency of the plurality of acoustic waves transmitted.

14. The system of claim 9, wherein the receiver is oriented generally collinear with a direction of propagation of the plurality of acoustic waves transmitted from the transducer probe.

15. The system of claim 9, wherein the receiver is positioned coaxially in relation to the transducer probe.

16. The method of claim 1, orientating a receiver collinear to a direction of propagation of the plurality of acoustic waves, the receiver operable to measure the variation in the magnetic field.

* * * * *